United States Patent [19]

Osterholm et al.

[11] Patent Number: 5,085,630

[45] Date of Patent: * Feb. 4, 1992

[54] OXYGENATED FLUOROCARBON NUTRIENT SOLUTION

[75] Inventors: Jewell L. Osterholm, Radnor; Glenn D. Frazer, Wynwood, both of Pa.

[73] Assignee: Thomas Jefferson University, Philadelphia, Pa.

[*] Notice: The portion of the term of this patent subsequent to Jul. 19, 2000 has been disclaimed.

[21] Appl. No.: 507,361

[22] Filed: May 21, 1990

Related U.S. Application Data

[60] Division of Ser. No. 333,658, Apr. 5, 1989, Pat. No. 4,981,691, and a continuation-in-part of Ser. No. 238,982, Aug. 24, 1988, Pat. No. 4,840,617, Ser. No. 183,536, Apr. 14, 1988, Ser. No. 428,900, Sep. 30, 1982, Pat. No. 4,758,431, and Ser. No. 582,961, Feb. 23, 1984, Pat. No. 4,686,085, which is a division of Ser. No. 428,850, Sep. 30, 1982, Pat. No. 4,445,500, which is a division of Ser. No. 354,346, May 19, 1989, Pat. No. 4,445,886, which is a continuation-in-part of Ser. No. 139,886, Dec. 30, 1987, Pat. No. 4,378,797, said Ser. No. 428,900, is a division of Ser. No. 354,346, , said Ser. No. 428,850, is a division of Ser. No. 139,886.

[51] Int. Cl.$^5$ .............................................. A61M 1/00
[52] U.S. Cl. ...................................... 604/28; 424/680; 424/422; 604/51; 604/21
[58] Field of Search ..................... 604/28, 21; 424/680

[56] References Cited

U.S. PATENT DOCUMENTS

| | | | |
|---|---|---|---|
| 4,393,863 | 7/1983 | Osterholm | 604/28 |
| 4,445,500 | 1/1984 | Osterholm | 604/28 |
| 4,445,887 | 1/1984 | Osterholm | 604/28 |
| 4,981,691 | 1/1991 | Osterholm | 424/422 |

Primary Examiner—C. Fred Rosenbaum
Assistant Examiner—Chalin Smith
Attorney, Agent, or Firm—Woodcock Washburn Kurtz Mackiewicz & Norris

[57] ABSTRACT

The invention provides novel improved oxygenated fluorocarbon nutrient solutions for treatment of hypoxic-ischemic neurologic tissue in mammals. The invention also provides methods of making such nutrient solution and methods of administering them.

8 Claims, No Drawings

OXYGENATED FLUOROCARBON NUTRIENT SOLUTION

REFERENCE TO RELATED APPLICATIONS

This is a division of application Ser. No. 333,658, filed Apr. 5, 1989, now U.S. Pat. No. 4,981,691 issued on Jan. 1, 1991, which is a continuation-in-part of Ser. No. 238,982, filed Aug. 24, 1988, now U.S. Pat. No. 4,840,617 entitled "Cerebral and Lumbar Perfusion Catheterization Apparatus for Use in Treating Hypoxic/Ischemic Neurologic Tissue" and is also a continuation-in-part of application Ser. No. 183,536, filed Apr. 14, 1988, entitled "Extravascular Circulation of Oxygenated Synthetic Nutrients to Treat Tissue Hypoxic and Ischemic Disorders".

This application is a continuation-in-part of Ser. No. 428,900, filed Sept. 30, 1982, now U.S. Pat. No. 4,758,431, entitled "Stroke Treatment Utilizing Extra Vascular Circulation of Oxygenated Synthetic Nutrients to Treat Tissue Hypoxic and Ischemic Disorders", and is also a continuation-in-part of Ser. No. 582,961, filed Feb. 23, 1984 of the same title, now U.S. Pat. No. 4,686,085. Ser. No. 582,961 is, in turn, a division of Ser. No. 428,850 filed Sept. 30, 1982, now U.S. Pat. No. 4,445,500, which along with Ser. No. 428,900 are both, in turn, divisions of Ser. No. 354,346, filed May 19, 1989, now U.S. Pat. No. 4,445,886 and which, in turn, is a continuation-in-part of Ser. No. 139,886, filed Dec. 30, 1987 (now U.S. Pat. No. 4,378,797), all of which are incorporated herein by reference as if set forth in full.

In addition, the present application is related to the following issued United States Patents, all of which are incorporated herein by reference as if set forth in full and all of which are divisions of one or the other of the aforementioned Ser. Nos. 139,886 and 354,346:

Ser. No. 06/275,117 filed Jun. 18 1981 (which was a division of 06/139,886), now U.S. Pat. No. 4,445,514 entitled "Extra Vascular Circulation of Oxygenated Synthetic Nutrients to Treat Tissue Hypoxic and Ischemic Disorders";

Ser. No. 06/275,116 filed Jun. 18, 1981 (which is a division of 06/139,886), now U.S. Pat. No. 4,393,863, entitled "Extra Vascular Circulation of Oxygenated Synthetic Nutrients to Treat Tissue Hypoxic and Ischemic Disorders";

Ser. No. 06/428,687 filed Sep. 30, 1982 (which was a division of 06/354,346), now U.S. Pat. No. 4,450,841, entitled "Stroke Treatment Utilizing Extra Vascular Circulation of Oxygenated Synthetic Nutrients to Treat Tissue Hypoxic and Ischemic Disorders";

Ser. No. 06/428,682, filed Sep. 30, 1982 (which was a division of 06/354,346), now U.S. Pat. No. 4,445,887, entitled "Stroke Treatment Utilizing Extra Vascular Circulation of Oxygenated Synthetic Nutrients to Treat Tissue Hypoxic and Ischemic Disorders";

Ser. No. 06/428,685, filed Sep. 30, 1982 (which was a division of 06/354,346), now U.S. Pat. No. 4,446,154, entitled "Stroke Treatment Utilizing Extra Vascular Circulation of Oxygenated Synthetic Nutrients to Treat Tissue Hypoxic and Ischemic Disorders";

Ser. No. 06/428,686, filed Sep. 30, 1982 (which was a division of 06/354,346), now U.S. Pat. No. 4,446,155, entitled "Stroke Treatment Utilizing Extra Vascular Circulation of Oxygenated Synthetic Nutrients to Treat Tissue Hypoxic and Ischemic Disorders";

Ser. No. 06/428,899, filed Sep. 30, 1982 (which was a division of 06/354,346), now U.S. Pat. No. 4,451,251, entitled "Stroke Treatment Utilizing Extra Vascular Circulation of Oxygenated Synthetic Nutrients to Treat Tissue Hypoxic and Ischemic Disorders";

Ser. No. 06/428,898, filed Sep. 30, 1982 (which was a division of 06/354,346), now U.S. Pat. No. 4,445,888, entitled "Stroke Treatment Utilizing Extra Vascular Circulation of Oxygenated Synthetic Nutrients to Treat Tissue Hypoxic and Ischemic Disorders"; and Ser. No. 06/428,850, filed Sep. 30, 1982 (which was a division of 06/139,886), now U.S. Pat. No. 4,445,500, entitled "Stroke Treatment Utilizing Extra Vascular Circulation of Oxygenated Synthetic Nutrients to Treat Tissue Hypoxic and Ischemic Disorders".

FIELD OF THE INVENTION

This invention relates in general to the field of treatments for hypoxic/ischemic neurologic tissue arising from cerebral vascular accident and more particularly to the field of treatments for such tissue that involve circulation of oxygen carrying synthetic liquids through the neurologic tissue.

BACKGROUND OF THE INVENTION

"Stroke" or focal cerebral ischemia presents an extremely complex patho-physiological problem. Stated most simply, cerebral ischemia is the reduction or loss of blood flow to all or part of the brain with a subsequent reduction or loss of oxygen and substrate delivery to the tissue As a cause of death, stroke ranks third after heart disease and cancer. When not lethal, it is associated with a type of morbidity which can ruin lives, leaving patients unable to cope with daily existence and imposing a heavy burden on the family and society. The disease's economic impact is staggering: for the year 1976, direct and indirect (lost wages) costs have been estimated to be 7.4 billion dollars. Accordingly there is an enormous need for providing a effective treatments for this disease.

SUMMARY OF THE INVENTION

The present invention provides novel improved fluorocarbon nutrient solution for circulation through cerebrospinal fluid pathways, and methods for using the novel nutrient formulation to treat central nervous tissue hypoxic-ischemic conditions.

Applicants have recognized that there is a therapeutic time window through which neuron can be reached and resuscitated. The method of the present invention is designed to bypass obstructed vascular circulation and deliver cerebral metabolic needs through an alternate cerebral spinal fluid (CSF) circulation portal. Since particle size exerts a major influence in brain penetration from CSF, the method of the present invention is hypothesized to permit diffusion of oxygen, glucose, electrolytes and essential amino acids into ischemic neural tissue when presented in abundance in the cerebral spinal pathway. Thus, a rapidly exchanging cerebral spinal fluid perfusion system is provided to amply supply these materials and, at the same time, remove metabolic waste. The cerebrospinal fluid (CSF) pathway system, which intimately bathes and permeates brain and spinal cord tissues, constitutes a unique anatomical relationship within the body. Although it has some similarities to systemic lymphatics its anatomical arrangement differs considerably from that of lymph. Indeed, this system has been named the "third circulation". Due to the extensive area of CSF-tissue contact over the cerebral and cord surfaces, in the miniature Virchow-Robins spaces, and cerebral ventricles, the cerebrospinal fluid system constitutes a vast, complex and intimate therapeutic avenue for access to central nervous tissue. Excepting certain infections and neoplasms where the cerebrospinal fluid is now utilized as a treatment conduit, the cerebrospinal fluid system has not been otherwise widely exploited as an easily accessible therapeutic route and has never been used as a continuous therapeutic diagnostic circulation system in man. The present invention is predicated on the recognition that, when regional cerebral blood flow is interrupted, such as after major stroke, or is otherwise seriously impeded by profound vaso-spastic states, the cerebrospinal fluid pathway actually represents the only practical and viable anatomical route by which these tissues may be readily treated. This results from the fact that the usual vascular delivery system is either occluded or non-functional, and thus tissues within affected territories cannot be properly served.

In accordance with the present invention, essential cellular substrates are delivered to beleaguered ischemic brain regions by utilizing the "back door" cerebrospinal fluid delivery route. Accordingly the present invention provides a novel nutrient emulsion for penetration into regions suffering vascular deprivation.

It has been found that the cerebrospinal fluid to brain relationship is not characterized by the rigid and highly selective barrier mechanism which are present at the blood-brain interface. Thus, the penetration rate of materials from cerebrospinal fluid regions to the brain relate largely to small molecular size, that is, small substances penetrate deeply while large molecules move slowly into brain substance. Although entry rates are generally inversely proportional to molecular weight, penetration is also influenced by lipid solubility and the molecular configuration of the penetrating substance. Accordingly, the present invention provides a nutrient emulsion containing essential brain nutrients including selected electrolytes, having a relatively low molecular size which, in accordance with the methods of the present invention, are caused to relatively freely diffuse from either the ventricular or subarachnoid fluid regions into the brain matter to be treated. Accordingly, the present invention provides novel nutrient emulsion which has been purified, balanced and perfected to fall within narrow phyliologic limits while nonetheless providing the desired nutritional characteristics referred to above.

The present invention also provides novel methods for treating hypoxic-ischemic neurologic tissue by circulating the oxygenated nutrient emulsion through cerebrospinal fluid pathways, particularly those pathways which contact brain and spinal cord tissue. According to these methods, treated tissues exhibit a substantially improved ability to resist and/or repair damage which would otherwise result from vascular occlusion. In accordance with the preferred method of the present invention, the novel oxygenated nutrient emulsion is circulated through this cerebrospinal fluid route by injecting it into brain vesicles and withdrawing it from the cisterna magna or the spinal subarachnoid space to nourish and to treat central nervous tissues. In other instances the fluid may be injected into the subarachnoid space and withdrawn from another subarachnoid position. The preferred embodiment oxygenate nutrient emulsion should be circulated to tissues to be treated in amounts sufficient to provide adequate gas exchange.

The formulation of the nutrient solution of the present invention has several unexpected advantages over other formulation heretofore known. It was discovered by the inventors that there is a relationship between the relative viscosity of the nutrient solution and its ability to perfuse the cat brain. It was found that there is a substantial reduction in the pressure needed to perfuse these solutions through a fixed resistance with increasing dilution, even at flow rates as low as one milliliter per minute. This discovery, coupled with the greater oxygen carrying capacity of bis-perfluorobutyl ethylene, has made it possible to use a lower concentration of perfluorocarbon in the nutrient solution of the invention. The nutrient solution of the invention which contains bis-perfluorobutyl ethylene has a 25% greater oxygen carrying capacity than that of a prior nutrient solution made with perfluorodecalin, Bell et al., Neurology 37: 133, 1987. The formulation of the invention is thus more viscous and relatively easier to perfuse. It has also been found that providing an electrolyte profile and osmotic pressure mimicking the cerebrospinal fluid of the mammal also improves the efficacy of the nutrient solution. Further, the exclusion of four amino acids, glutathione, cysteine, ornithine and glutamine, from the group of amino acids included in the nutrient solution, and the inclusion of sodium bicarbonate in amounts sufficient to increase the buffering capacity of the nutrient solution to more closely resemble cerebrospinal fluid of the mammal were also discovered to contribute to the improved efficacy of the nutrient solution of the present invention.

DETAILED DESCRIPTION OF THE INVENTION

The synthetic oxygenated fluorocarbon nutrient solution of the invention is comprised of carefully formulated components which, to the extent possible while maintaining desired therapeutic activity, mimic the physical and chemical characteristics of natural cerebrospinal fluid. Generally, tissues and cells will not fair well if exposed to large volumes of non-physiologic ionic solutions. Accordingly, it has been recognized that appropriate electrolyte compositions at the tissue level are indispensable when it is considered that the circulatory method of the present invention would otherwise result in the washing and the dilution of electrolytes from the region even after short terms of circulation, to the detriment of cell membrane functions. Accordingly, in accordance with the preferred embodiment of the present invention, sodium, potassium, calcium, magnesium, and chloride ions are carefully balanced in the nutrient emulsion of the present invention to thereby create, to the degree possible, normal extracellular compositions. The present invention also provides a non-aqueous oxygen transfer component for selectively combining with oxygen and for transferring oxygen to the tissues to be treated. Numerous compounds are known to the art which are characterized by having a high solvent property for oxygen, carbon dioxide, and other gases. The preferred non-aqueous oxygen transfer component of the preferred nutrient liquid should exhibit when so charged, oxygen vapor pressure ranges of above 400, and preferably 600, Torr. Such oxygen transfer components should similarly not have in themselves high vapor pressure which would boil at body temperatures, nor have viscosities which are difficult if not possible to emulsify. Generally, the preferred compounds for use as non-aqueous oxygen transfer components are fluorocarbon polymers, such as perfluorocarbons, perfluorinated alkyl polyethers, fluoroethers, fluoramines, etc. While compounds within these groups range in molecular weight from 250 to 7000, their selection for use as non-aqueous transport components are based upon the combination of features of the proper vapor pressure, molecular weight, viscosity, and emulsifiability, emulsionstability and tissue distribution.

Not only do fluorocarbons possess these unique physical gaseous properties but they are for the most part non-toxic. The main acute toxicity has been found to reside in free fluoride ion accumulation which occurs mainly from sonication. See, Clark et al., Fed. Proc. 34, pp. 1468-1477 (1979). The free ion can, however, be removed by repetitive dialysis and the emulsion thereby rendered physiologically acceptable. Accordingly, the preferred embodiment nutrient liquid of the present invention, which has been dialyzed and filtered through a millipore filter, has evidenced no toxicity either in short term or long term use during circulation through cerebrospinal pathways of animals. One chief advantage of the CSF circulation route is that most or all the nutrient liquid can be removed by washing at the time of treatment termination. In this way long term cellular retention as previously noted for liver and reticuloendothelial cells in vascular circulations of oxygenating liquids may be avoided.

In the preparation of the preferred nutrient liquid, an important factor in producing an acceptable nutrient liquid is the achievement of an acceptable final osmotic pressure. The osmotic pressure of the nutrient liquid will depend upon the amount of the emulsification component, the particle size of the fluorocarbon, and the ionic composition of the aqueous nutrient component. In accordance with the preferred method of preparing the nutrient liquid of the present invention, toxic emulsification components should be removed by dialysis. Fluorocarbon particle size will be controlled by sonification time and filtering, while the ionic composition of the aqueous nutrient component will be carefully adjusted to produce a nutrient liquid possessing desired osmotic characteristics. If desired, a final osmotic tuning may be accomplished in accordance with the method of the present invention by adding ascorbic acid to the nutrient liquid.

In order to provide fully successful treatment of ischemic tissues, it is desirable to provide nutrient liquid for circulation around those tissues which will compensate for relative or complete deficiencies of blood transport metabolites. In addition to oxygen, other tissue metabolic requirements include glucose, amino acids, ions, hormones, vitamins, etc. While in temporary treatment conditions, it may be suitable to temporarily omit one or more vitamin, hormone, ion, or amino acid, for prolonged treatment and to produce the most desirable results, it is preferred to provide substantially all of the above mentioned metabolites in the preferred nutrient liquid. It is at least desirable to provide in the nutrient liquid all components necessary to support aerobic metabolism which will be available within the medium for use at cellular levels. Glucose deprivation of central nervous system tissue causes a serious cellular metabolic deficiency, as does the same degree of oxygen deficiency. Accordingly, by providing a total and finely adjusted mixture that has all the necessary components for total cell survival, an extremely efficient and therapeutic liquid material is provided which is ideal for circulation through the cerebrospinal pathways.

The nutrient solution of the invention is made according to the procedure disclosed in U.S. Pat. No. 4,446,155, particularly Example 1 therein. In general, the emulsifier lecithin is mixed with artificial cerebrospinal fluid (i.e. water buffered with electrolytes), usually in a blender or other apparatus to ensure even dispersion of the lecithin in the artificial cerebrospinal fluid. The perfluorocarbon bis-perfluorobutyl ethylene (contained in Therox TM, DuPont, Wilmington, Del.) is slowly added to cooled cerebrospinal fluid and the entire mixture is sonicated in a sonifier cell disrupter to reduce particle size and then dialyzed and filtered to remove free fluoride ions. Then the osmolarity and pH of the emulsion are then adjusted to the appropriate ranges. The emulsion is then sterilized by filtering. Just before using, glucose, albumin and amino acids are added and the nutrient solution is oxygenated by bubbling oxygen through the mixture. An illustration of the preferred method and composition of the nutrient solution of the invention can be found in Example 1.

The nutrient solution of the invention is preferably administered according to the method set forth in U.S. Pat. No. 4,445,500 which is specifically incorporated as if fully set forth herein. The nutrient solution of the invention is perfused tissue areas by injection of the nutrient solution at a first point in the cerebrospinal pathway and substantially continuously withdrawing fluid from the cerebrospinal pathway at a second point which is selected to create a circulation of the nutrient solution in the vicinity of hypoxic-ischemic tissue to metabolically sustain the tissue during treatment.

EXAMPLE 1

| OFNS Formula 3003A | |
|---|---|
| Component | Amount/Liter Emulsion |
| BBFC* | 151.370 gm |
| Lecithin | 10.500 gm |
| NaCl | 6.674 gm |
| KCl | 0.199 gm |
| CaCl2.2H2O | 0.198 gm |
| NaHCO3 | 1.359 gm |
| MgCl2.6H2O | 0.037 gm |
| MgSO4.7H2O | 0.288 gm |
| NaHPO4.7H2O | 0.200 gm |
| Glucose | 0.900 gm |
| Albumin | 18.000 gm |
| Water for inj. QS to | 1000.000 ml |
| Amino Acids & Precursor | Milligram wt. per liter emulsion |
| Glycine | 0.8 |
| L-lysine HCl | 3.7 |
| L-tryptophan | 2.0 |
| L-alanine | 2.3 |
| L-serine | 2.6 |
| L-threonine | 3.0 |
| L-arginine | 3.5 |
| L-leucine | 2.6 |
| L-valine | 2.3 |
| L-phenylalanine | 3.3 |
| L-tyrosine | 3.6 |
| L-histidine | 3.1 |
| L-methionine | 1.5 |
| L-isoleucine | 2.6 |
| Alpha-ketoglutaric acid | 7.3 |

*BBFC stands for bis-perfluorobutyl ethylene(Therox from DuPont)

The above listed components are mixed according to the method of U.S. Pat. No. 4,450,841, particularly Example 1 therein, with lecithin substituted for the emulsifier in that example.

EXAMPLE 2

Efficacy Study of Oxygenated Fluorocarbon Nutrient Solution Formula of Example 1

Focal cerebral ischemia was produced by permanent left middle cerebral artery occlusion in fourteen animals under alphachoralose anesthesia. They were assigned to either an untreated control group or to a group treated by ventriculo-cisternal perfusion with oxygenated fluorocarbon nutrient solution Formula 3003A, the nutrient solution of Example 1, according to a previously determined randomization schedule. Following the production of the ischemic insult, the laboratory personnel were informed as to whether the animal was to be treated or not. If treated, treatment by ventriculo-cisternal perfusion with the oxygenated fluorocarbon nutrient solution of Example 1 began after 90 minutes had elapsed from the production of the insult. For perfusion with the nutrient solution, the inflow catheter was inserted into the left lateral cerebral vantricle and the outflow catheter was inserted into the cisterna magna.

Of the fourteen experiments attempted, nine fulfilled all protocol requirements and were included in the final analysis. Of the remaining five, four did not meet the criteria for vascular clip placement on the MCA. The other died before completing the experiment because of an autopsy proven collapsed lung, presumably caused by too vigorous trans-tracheal suctioning.

The results of the treated animals were compared to the previous results of a feasibility study using the formula of Example 1, and no differences were detected. As the protocol used was the same, the results were pooled and compared against the control animals. The infarct sized of the perfused and untreated animals, (Table 4), were compared using the Mann-Whitney U test, for both methods of determination, (tetrazolium and standard histopathological examination). There were statistically significant reductions in infarct volume in the treated group as compared to control, by either method of evaluation: $p<0.05$ for the tetrazolium technique and $p<0.01$ using standard histopathological techniques.

Of the four perfused animals which did not adhere to protocol, three had no or very small infarcts. Only the animal which was found to have the clip on both the MCA and the internal carotid artery had a substantial infarct. The unperfused (control) protocol failure was due to failure to clip the middle cerebral artery. As should be expected, it was subsequently found not to have an infarct.

TABLE 4

Comparison of Infarct Sizes Following L Middle cerebral artery occlusion in Cats
Untreated vs. Ventriculo-cisternal Perfusion with Oxygenated Fluorocarbon Nutrient Solution of Example 1

| Exp # | % Infarct of the Cerebrum | |
|---|---|---|
| | Tetrazolium | Histopathology |
| Untreated | | |
| 2823 | 12.16 | 10.05 |
| 2827 | 17.23 | 10.90 |
| 2828 | 28.20 | 12.95 |
| 2833 | 4.12 | 0.88 |
| 2836 | 12.12 | 8.14 |
| 2838 | 0.00 | 0.13 |
| Mean | 12.13 | 7.18 |
| Treated | | |

TABLE 4-continued

Comparison of Infarct Sizes Following L Middle cerebral artery occlusion in Cats
Untreated vs. Ventriculo-cisternal Perfusion with Oxygenated Fluorocarbon Nutrient Solution of Example 1

| Exp # | % Infarct of the Cerebrum | |
|---|---|---|
| | Tetrazolium | Histopathology |
| 2818 | 0.77 | 0.68 |
| 2819 | 0.27 | 0.00 |
| 2820 | 0.00 | 0.00 |
| 2822 | 0.13 | 0.00 |
| 2825 | 0.15 | 0.00 |
| 2832 | 1.09 | 1.90 |
| 2837 | 0.14 | 0.00 |
| Mean | 0.36 | 0.37 |
| Prob. | $p<0.05$ | $p<0.01$ |

Brain electrical activity was monitored with a two-channel Neurotrac cerebral function monitor with bilateral, bipolar recording electrodes The electrical power (Fast Fourier Transform) was computed for each hemisphere in total and for each of the standard frequency bands; alpha, beta, delta and theta. No significant differences could be detected, probably because of the degree of inter-animal variability and the overall suppression of the EEG by the anesthetic.

The arterial blood gases were controlled by adjusting respiration rate and volume, and by the administration of sodium bicarbonate. Plasma glucose was controlled by the administration of insulin for hyperglycemia and glucose for hypoglycemia.

Other physiological variables were compared between groups: blood pressure, heart rate, rectal temperature, and ICP. A two-way ANOVA with repeated measures was done on each variable, and no statistically significant differences were detected between treated and control animals for these variables.

However, there was noted a marked elevation in ICP in the untreated animals, which is not seen in the treated preparations. Closer examination of the data revealed that three of the six control animals had elevations of ICP greater than 10 mm Hg, whereas none of the treated group had an ICP higher than 8 mm Hg and averaged much lower. The non-normality of the data indicated the use of a non-parametric statistical test. When the final ICP readings of the treated vs. control were compared using the Mann-Whitney U test, the difference was significant at the $p<0.01$ level. This is an extremely important treatment effect because of the strong clinical correlation between elevated ICP following cerebral ischemia in man, and mortality and morbidity.

These data also lend reassurance to the safety of the oxygenated fluorocarbon nutrient solution, in that there were no detectable differences in the mean arterial blood pressure and heart rate between the groups. There appears to be no effect of the technique on the central nervous system cardiovascular centers controlling these variables, even though the perfusate outflow temperature is low, (approximately 1 or 2 degrees above room temperature), and hypothermia has been associated with cardiac arrhythmias.

Blood Chemistries and Hematology $PCO_2$ and bicarbonate levels of the oxygenated fluorocarbon nutrient solution were checked on the ABL-30 blood gas analyzer (Radiometer). Perfusion was not allowed to begin until the values were within the protocol limits.

The oxygenated fluorocarbon nutrient solution was sampled for gas analysis before entering the animal every 30 minutes, and corresponding outflow sample of oxygenated fluorocarbon nutrient solution was taken every hour, if possible.

EXAMPLE 3

Recovery Experiments

After determining that oxygenated fluorocarbon nutrient solution Formula 3003A is efficacious in the permanent middle cerebral artery occlusion model of focal cerebral ischemia in the cat, a preliminary series of recovery experiments were embarked upon to demonstrate the safety and lack of acute toxicity of ventriculocisternal perfusion with oxygenated fluorocarbon nutrient solution of Example 1. Two animals underwent ventriculocisternal perfusion without receiving a cerebral ischemic insult and two underwent left middle cerebral artery occlusion ninety minutes before the start of treatment. The inflow catheter was inserted into the left lateral cerebral ventricle and the outflow catheter was inserted into the cisterna magna through the atlantooccipital membrane. The experiments were conducted under isoflurane anesthesia. Because of time and personnel constraints, the number of days that the animals were allowed to survive before sacrifice was shortened to ten days for the unstroked and two days for the stroked animals.

All animals were perfused without elevations in the ICP. The unstroked animals were perfused for eighteen hours on the following rate schedule:
1) 14 hours at 108 ml/hr.
2) 1 hour at 120 ml/hr.
3) 1 hour at 90 ml/hr.
4) 1 hour at 60 ml/hr.
5) 1 hour at 30 ml/hr.

At the cessation of perfusion with oxygenated fluorocarbon nutrient solution, the animals were perfused with Ringers solution (at a delivery pressure less than 5 mm Hg) until the cisternal exit fluid ran clear, (less than five minutes in each case). The animals wounds were then closed, and anesthesia was withdrawn. Both of the unstroked animals awoke from the anesthesia within two hours, and were neurologically intact. However, both were disinterested in food and water for the first four to give days, a normal response of the cat to physical injury.

The first perfused, unstroked animal (#2841) ate a large amount of food for the first time on recovery day five, but within a few hours was observed to be unreactive to stimuli with labored breathing, and died before ventilatory support could be instituted. Approximately 10-20 ml of vomitus was aspirated from the oral cavity and pharynx. Autopsy revealed a pneumothorax and an inflamed larynx, consistent with acute aspiration of gastric contents. Apart from a small hemorrhagic cortical lesion at the site of the ventriculostomy, the brain appeared grossly normal. Histopathological examination of the necropsy samples, with cellular and myelin detail using the classic group of tissue strains, confirmed the gross finding of the small surgical infarct in the brain and found all other tissue samples to be normal.

The other unstroked animal, (#2842), recovered completely from the effects of the surgery and anesthesia and lived until sacrifice on recovery day 10. Autopsy revealed no gross abnormality, a finding confirmed on histopathological examination.

The first animal which had an ischemic insult, #2843, was perfused for fourteen hours at 180 ml/hr, except for a short period (a few minutes) where the rate was reduced to zero while a blockage of the outflow system was resolved. After fourteen hours of perfusion, the rate was dropped to 120 ml/hr and allowed to equilibrate for 30 minutes. Inflow and outflow samples were taken to determine the effect of the rate on the in-out differences pH and oxygen. As the differences were comparable to those found in the unstroked animals, the rate was further reduced to 90 ml/hr. This process was repeated until the flow was finally stopped after a total of sixteen hours and 35 minutes of persuion. Ringers solution was again used to flush the remaining oxygenated fluorocarbon nutrient solution from the subarachnoid space.

The wounds were then sewn up, and the animal withdrawn from anesthesia. The animal was fully conscious within six hours after discontinuation of anesthesia. By 4 hours after onset of the ischemic insult, the animal's reflexes were found to be normal except for hyperreactivity and increased tone in the right hindlimb. The animal did not stand and walk spontaneously, but did sit in a normal position. The animal was sacrificed according to protocol, the brain removed and selected other tissues sampled for histopathological examination.

The brain appeared grossly normal with no apparent swelling, and was normal in texture The lungs showed signs of atelectasis and were congested, presumed secondary to a preexisting infection. (Notification by the animal supplier, Liberty Laboratories, of the existence of a respiratory problem in the batch of animals from which this animal was chosen, came after the initiation of the experiment.) The right ventricle of the heart was slightly enlarged as was the liver, both signs of right sided heart failure, secondary to the pneumonia. Histopathological examination of the brain revealed no abnormalities, and the other tissues sampled appeared normal.

The second animal to be stroked, treated and recovered was perfused for twelve hours at 180 ml/hr, until problems with the outflow catheter occurred. The rate was dropped to 160 ml/hr for the next two hours, at which point the outflow catheter was removed and the outflow allowed to run freely from the incision in the atlanto-occipital membrane. The rate was then dropped over the next three hours in 30 ml/min decrements every thirty minutes. Ringers solution was again used to rinse the sub-arachnoid space as in the previous experiments. The animal's wounds were then sewn up and the animal withdrawn from the anesthesia.

Post-operative recovery was slower in this animal than in the previous three, with twenty hours elapsing before returning to an aware alert state. Neurologically all reflexes were intact, but weakness was noted in both hind-limbs and the right fore-limb. However, the animal did walk spontaneously, but with splaying of the limbs on the right side.

The animal was sacrificed according to protocol, and the brain removed and other tissues sampled for analysis. On gross examination the brain was normal in texture with no obvious swelling, but the pial veins were distended on the surface of the left hemisphere, and there was an area of pallor on the temporal lobe. Aside from some small atelectatic areas in the lungs, all of the organs examined appeared grossly normal.

Histopathological examination revealed a left cortical infarct of moderate extent, (4.0% of the cerebral volume), which was consistent with the neurologic status of the animal. No pathologic changes were noted in the other tissues.

SIGNIFICANCE

The optimized formulation of oxygenated fluorocarbon nutrient solution of Example 1 was tested for efficacy in the permanent middle cerebral artery occlusion model in the cat. Treatment with this oxygenated fluorocarbon nutrient solution produced a statistically significant reduction in cerebral infarct size when compared to untreated controls at 20 hours after insult. No apparent acute toxic effects on the animals neural of systemic physiology were found. Histopathological examination of the bran and meninges found no toxic responses following 18 hours of exposure to the oxygenated fluorocarbon nutrient solution, at appreciable flow rates.

From results of the recovery studies, perfusion of normal cats was without observable effect on the neurologic and physiologic status of the animal, up to ten days after the exposure. The results from the stroked, treated and recovered animals are consistent with the improvements seen in the shorter studies, with both animals sustaining only mild neurological deficits. Neither of these animals demonstrated a progressive worsening of their condition after the withdrawal of therapy.

The possible mechanism by which this technique preserves the tissue after a permanent vessel occlusion are numerous but three that are likely are: 1) that the perfusion supports the tissue for enough time to allow collateral circulation to improve to the point of providing functional supply, 2) the residual emulsion in the extravascular fluid spaces is assisting in the transfer of oxygen and nutrients from adjacent normally perfused areas, and 3) that the perfusion interrupts the normal pathophysiological cascade, removing toxic metabolites, and normalizing the ionic microenvironment, thus preventing secondary brain damage, (13). Each of these mechanisms could be operating to some degree. These findings, in combination with the results indicating efficacy, suggest that this nutrient solution of the invention (in Example 1) could have clinical utility in the treatment of acute focal cerebral ischemia, a disease for which there is no currently accepted efficacious treatment.

We claim:

1. A method of treating hypoxic-ischemic neurologic tissue in mammals, comprising:
   (a) providing a physiologically acceptable synthetic oxygenatable fluid comprising bis-perflurobutyl ethylene with a synthetic electrolyte-containing cerebrospinal aqueous fluid to produce a physiologically acceptable emulsion;
   (b) oxygenating said oxygenatable fluid to produce an oxygenated fluid;
   (c) injecting a substantially continuous stream of said oxygenated fluid into the cerebrospinal fluid pathway, at a first injection point;
   (d) substantially continuously withdrawing fluid from said cerebrospinal fluid pathway at a second point which is selected to create a circulation of said oxygenated fluid in the vicinity of said ischemic tissue, whereby ischemic neurologic tissue will be oxygenated and otherwise nourished by said fluid.

2. The method of claim 1 wherein said first point is within a cerebral ventricle.

3. The method of claim 2 wherein said second point is within the lateral ventricle.

4. The method of claim 1 wherein said second point is within a subarachnoid space.

5. The method of claim 1 wherein said second point is within a cerebral cistern.

6. The method of claim 5 wherein said cerebral cistern is the cisterna magna.

7. The method of claim 4 wherein said subarachnoid space is a spinal subarachnoid space.

8. The method of claim 7 wherein said spinal subarachnoid space is a lumbar spinal subarachnoid space.

* * * * *